(12) United States Patent
Haar et al.

(10) Patent No.: US 9,119,581 B2
(45) Date of Patent: Sep. 1, 2015

(54) TAPE MAGAZINE FOR A HAND-HELD DEVICE

(71) Applicant: Roche Diagnostics Operations, Inc., Indianapolis, IN (US)

(72) Inventors: Hans-Peter Haar, Wiesloch (DE); Hans List, Hesseneck-Kailbach (DE); Bernd Roesicke, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 14/464,911

(22) Filed: Aug. 21, 2014

(65) Prior Publication Data

US 2014/0361112 A1 Dec. 11, 2014

Related U.S. Application Data (62) Division of application No. 13/049,979, filed on Mar. 17, 2011, now Pat. No. 8,815,154, which is a division of application No. 11/376,839, filed on Mar. 16, 2006, now abandoned.

(30) Foreign Application Priority Data

Mar. 18, 2005 (DE) .......................... 10 2005 013 685

(51) Int. Cl.
*G01N 21/00* (2006.01)
*A61B 5/145* (2006.01)
(Continued)

(52) U.S. Cl.
CPC ......... *A61B 5/14532* (2013.01); *A61B 10/0045* (2013.01); *B65H 16/00* (2013.01); *B65H 18/08* (2013.01); *G01N 33/48764* (2013.01); *G01N 35/00009* (2013.01); *A61B 2562/0295* (2013.01); *Y10T 436/2575* (2015.01)

(58) Field of Classification Search
CPC .............................. A61B 5/1411; B29C 66/71
See application file for complete search history.

(56) References Cited

U.S. PATENT DOCUMENTS 3,602,448 A 8/1971 Muensterer
3,620,678 A 11/1971 Guigan et al.
(Continued)

FOREIGN PATENT DOCUMENTS

CA 2516490 5/2004
CA 2511179 A 6/2005
(Continued)

OTHER PUBLICATIONS

JP 2009-235544 A English Language Machine Translation.
(Continued)

*Primary Examiner* — Jyoti Nagpaul
(74) *Attorney, Agent, or Firm* — Roche Diabetes Care, Inc.

(57) ABSTRACT

The present invention concerns a tape magazine especially for a hand-held device for analyzing a body fluid with a test tape that can be unwound from a storage unit and wound onto a waste unit where the waste unit can be driven in order to wind forward the test tape. The invention provides that a lock which keeps the test tape under tension is integrated in the tape magazine at least on the storage unit. The present invention also concerns a hand-held device with such a tape magazine. The present invention also concerns a hand-held device with a mechanical drive for the test tape and a disposable hand-held device with polymer-based electronic components.

23 Claims, 4 Drawing Sheets (51) Int. Cl.
*A61B 10/00* (2006.01)
*G01N 33/487* (2006.01)
*G01N 35/00* (2006.01)
*B65H 16/00* (2006.01)
*B65H 18/08* (2006.01)

(56) References Cited

U.S. PATENT DOCUMENTS

| | | | |
|---|---|---|---|
| 3,728,081 | A | 4/1973 | Bidanset |
| 4,001,887 | A | 1/1977 | Platt et al. |
| 4,218,421 | A | 8/1980 | Mack, Jr. et al. |
| 4,883,642 | A | 11/1989 | Bisconte |
| 7,212,719 | B2 | 5/2007 | Fujiwara et al. |
| 7,641,857 | B2 | 1/2010 | Clemens et al. |
| 2005/0201897 | A1 | 9/2005 | Zimmer et al. |
| 2005/0232815 | A1 | 10/2005 | Ruhl et al. |
| 2005/0245845 | A1 | 11/2005 | Roe et al. |
| 2006/0079811 | A1 | 4/2006 | Roe et al. |
| 2006/0099108 | A1 | 5/2006 | List et al. |
| 2006/0173380 | A1 | 8/2006 | Hoenes et al. |
| 2007/0173740 | A1 | 7/2007 | Chan et al. |
| 2008/0103415 | A1 | 5/2008 | Roe et al. |
| 2008/0286149 | A1 | 11/2008 | Roe et al. |
| 2009/0095641 | A1 | 4/2009 | List et al. |
| 2009/0321287 | A1 | 12/2009 | List et al. |

FOREIGN PATENT DOCUMENTS

| | | | |
|---|---|---|---|
| DE | 198 19 407 | A1 | 11/1999 |
| DE | 699 29 895 | T2 | 8/2006 |
| FR | 2 565 350 | A1 | 12/1985 |
| JP | 1986 26933 | Y2 | 12/1986 |
| JP | 1996 012149 | A | 1/1996 |
| JP | 1997 254507 | A | 9/1997 |
| JP | 202 019388 | A | 1/2002 |
| JP | 2003-038996 | A | 2/2003 |
| JP | 2003 510606 | A | 3/2003 |
| JP | 2003-300173 | A | 10/2003 |
| JP | 2003 338526 | A | 11/2003 |
| JP | 2004 291392 | A | 10/2004 |
| JP | 2004 326054 | A | 11/2004 |
| JP | 2006 070624 | A | 3/2006 |
| JP | 2006 511264 | A | 4/2006 |
| JP | 2009-513179 | A | 4/2009 |
| JP | 2009-235544 | A | 10/2009 |
| WO | 02100274 | A1 | 12/2002 |
| WO | 2004044571 | A1 | 5/2004 |
| WO | 2004047642 | A1 | 6/2004 |
| WO | 2004056269 | A1 | 7/2004 |
| WO | 2004057345 | A2 | 7/2004 |
| WO | 2007147494 | A2 | 12/2007 |

OTHER PUBLICATIONS

Japanese Patent Application No. 2009-235544 Office Action mailed Dec. 20, 2011 (translation-in-part).

Japanese Patent Application No. 2006-070624 Office Action mailed Mar. 30, 2010 (translation-in-part).

U.S. Appl. No. 11/283,079 to Roe et al., Office Action mailed Jul. 20, 2009.

TAPE MAGAZINE FOR A HAND-HELD DEVICE

CROSS-REFERENCE TO RELATED APPLICATIONS

The present application is a divisional of U.S. patent application Ser. No. 13/049,979, filed Mar. 17, 2011, pending, which is a divisional of U.S. patent application Ser. No. 11/376,839, filed Mar. 16, 2006, abandoned, which claimed priority to German Patent Application 10 2005 013 685.0, filed Mar. 18, 2005, all of which are hereby incorporated by reference in their entirety.

TECHNICAL FIELD

The invention concerns a tape magazine for a hand-held device for examining a body fluid comprising a test tape, a storage unit for unused test tape and a waste unit for used test tape where the waste unit is driven in order to wind forward the test tape.

BACKGROUND

In such tape magazines an unused section of test tape is pulled from a supply reel and guided over a receiving device where it takes up a sample of body fluid. Afterwards the section of test tape which is now used is wound onto a waste reel. A detection device which measures the sample and transfers the result of the measurement to an evaluation device is attached to the receiving unit.

Such tape magazines are preferably used in blood sugar measuring instruments for diabetics who depend on a continuous monitoring of their blood sugar values. The test tape allows a blood sugar test to be carried out inside the instrument after applying capillary blood for example from a finger pad. For this purpose a plurality of test sections or test fields are arranged consecutively on the test tape. An unused section of tape is moved into an active position by advancing the tape. Then the capillary blood is applied and analyzed. In order to simply dose very small amounts of blood and to position the test tape as exactly as possible relative to the detection device, the test tape is guided over a deflecting head inside the instrument. In this process there is a risk of erroneous measurements if the test tape slips off the deflecting head. For a successful measurement the test tape must remain at a well-defined position and rest against it evenly while maintaining a predetermined distance to the detection unit. This is necessary for at least as long as it takes to complete the measurement. Another challenge is that the test tape is very sensitive to contamination. Hence the unused area of the test tape should be spatially separated from the used area and also be screened from external influences which could impair the function of the test tape. Hence a direct drive coupling between the storage unit and the waste unit is very difficult.

Furthermore the hand-held devices of the prior art are designed for continuous use whereas the tape magazine is replaced. The hand-held devices are therefore relatively large and quite laborious to manufacture not least due to the complicated instrument technology.

SUMMARY

Hence an embodiment of the present invention is formed to provide a tape magazine which prevents malfunctioning due to slack tape.

An embodiment of the present invention is further is formed to provide a hand-held device which is compact and has a favorable design for manufacturing.

The combination of features stated in each of the independent patent claims is proposed. Embodiments and further developments of the invention are derived from the dependent claims.

The present invention provides a tape magazine apparatus for a hand-held device for analyzing a body fluid. The apparatus comprises a test tape, a storage unit formed for unused test tape, a waste unit formed for used test tape and to be driven in order to move forward the test tape from the storage unit, and an integrated brake that is formed to hold the test tape under tension between the storage and waste units.

The present invention provides a tape magazine apparatus for analyzing a body fluid. The apparatus comprises a test tape, a reel body for unused test tape and a reel body for used test tape, at least one reel body being driven in order to forward the test tape, and a hand-operated transport mechanism provided as a tape drive.

The present invention further provides a hand-held device for analyzing a body fluid. The device comprises a tape magazine, an analytical test tape located in the tape magazine, and device electronics based upon integrated polymer circuits.

Further, the present invention provides a method of dispensing a test tape for an analysis of body fluid. The method comprises providing a test magazine including a test tape, a storage unit formed for unused test tape, a waste unit formed for used test tape and to be driven in order to move forward the test tape from the storage unit, and an integrated brake, applying a brake force with the integrated brake to hold the test tape under tension between the storage and waste units, and actuating the test tape with a tensile force sufficient to move the test tape from the storage unit toward the waste unit.

Accordingly it is proposed that a brake that holds the test tape under tension is integrated into the tape magazine. This enables the required minimum tape tension to be maintained since the waste unit drive transports the test tape against this tension so that it is not pulled too far away from the storage unit or unintentionally wound off. This allows the test tape to be deflected at a well-defined position relative to the detection unit. In this process the minimum tape tension also prevents unintentional lateral displacement. The tape drive force should in any case be of a sufficient magnitude to overcome the effect of the braking means.

In particular, a braking force is applied to the storage unit which keeps the test tape under tension. This in particular prevents used test tape from being unintentionally wound off towards the application site. It also prevents areas of the test tape that have already been contaminated with blood from being pulled out of the tape magazine again which is an important hygienic advantage.

The braking means can exert a braking force directly on the test tape. Alternatively the braking means can act on a reel body for the test tape such that the test tape is indirectly braked. In the latter case no allowance has to be made for changes in the diameter of the tape spool. Furthermore, this does not apply additional mechanical stress to the test tape.

A simple embodiment provides that the braking means exert a constant braking force on the storage unit. This can be achieved by designing the braking means as a frictional element which in particular have a leaf spring as a frictional element. The braking means are formed by a seal which seals the storage unit at an opening for the test tape.

In a somewhat more elaborate embodiment the braking means act on the storage unit with a variable braking force. This enables the force required to pull out the test tape to increase to a lesser extent as the diameter of the supply spool decreases compared to the simple embodiment described above. In this connection it should be taken into consideration that the supply spool has a certain bearing friction which has to be overcome by the drive. Accordingly it is necessary to apply a torque which results from the momentary radius of the waste spool and the applied force to reel off the tape from the supply spool. Thus when the radius of the supply spool decreases with time, this force must increase. If the braking force decreases as a function of the tape tension, the overall increase in force can be kept lower.

An embodiment provides that the braking means have a deflector lever which is loaded with a braking force via a spring where the deflector lever deflects the test tape over a roller. As the tape tensile force decreases the deflector lever is unloaded. The deflector lever can for example be loaded with a leaf spring or pressure spring to exert the braking force and acts as a brake on a spool housing for the test tape.

Another improvement envisages that the braking force is not only modulated by the tape tension but also by the current spool diameter with the aid of a compensation mechanism so that the tape tension remains almost constant.

This object can be achieved with a compensation mechanism which has a spring-loaded rocker arm which probes the circumference of the tape spool wherein the spring loading decreases as the diameter of the tape spool decreases and the braking force is correspondingly reduced. Hence the tape tensile force remains constant.

In another embodiment a recoil locking device or recoil brake which acts in a form-fitting or frictional manner can be provided on the waste unit. If a recoil locking device is used as a locking mechanism, the drive for forwarding the test tape only has to overcome the friction of the storage unit which in particular spares the battery of the drive. This recoil safeguard should not act on the tape drive so that it is also effective when the tape magazine is removed from the hand-held device and prevents used tape from being unintentionally reeled out. The recoil locking device can be designed in a known manner as a safety catch which engages in gear teeth for example in the spool housing of the waste unit in such a manner that a form fit in the reverse direction prevents the waste unit from turning back. The waste unit is then restricted to the "wind on" direction of rotation. However, a frictional locking mechanism can also be provided. Various mechanisms are conceivable for this for example a wrap spring lock or a clamp roller freewheel.

The tape magazine has a housing which encloses the test tape, the storage unit and the waste unit. The storage unit should be accommodated in a storage space that is screened from influences that could impair the test tape. This can for example be achieved by a wall of the storage space forming an overlapping area with a wall of the housing with an opening for the test tape being formed along the overlapping area. This opening should be provided with at least one sealing agent or with one sealing means in order to protect the test tape from external influences.

The present invention also concerns a tape magazine for a test tape in which a hand-operated transport mechanism is provided as a tape drive. An actuating lever is provided for this which engages in an advancing element (e.g. capstan or index wheel) via a feed member, in particular a pawl, in such a manner that the test tape can be moved mechanically. A battery power supply is thus unnecessary. The energy required for the actual measuring process can be generated by the manual actuation and especially by means of an inductive generator or piezo-electrically and for example stored temporarily in a capacitor or high-performance capacitor (super-cap). The tape magazine also forms a hand-held device intended as a single-use article, a so-called disposable, which can be discarded after the test tape has been used due to the cost-effective construction.

The feed mechanism can for example be formed by a ratchet which engages in steps formed in the storage unit and/or waste unit. Such a construction is robust and simple to operate.

The test tape feed is synchronized by a perforation in such a manner that a test element is ready for a measurement when the lever is actuated at least once so that the measurement can be carried out particularly reliably and with great accuracy. Reference fields can be provided on the tape to further improve the feed accuracy.

Finally the present invention concerns a hand-held device which is directly formed by a tape mechanism and has instrument electronics, in particular a sensor unit, an evaluation unit and a display unit based on polymer electronics. Such a hand-held device can be constructed to be small and light, can be manufactured cost-effectively and can be used as a disposable unit.

In particular all disclosed embodiments of tape magazines and hand-held devices can be combined with one another. This applies especially to a hand-held device with electronic components based on polymer electronics combined with a mechanical drive for the test tape.

The invention is elucidated in more detail in the following on the basis of the embodiment examples shown in a schematic manner in the drawing.

DETAILED DESCRIPTION

Figure 1:
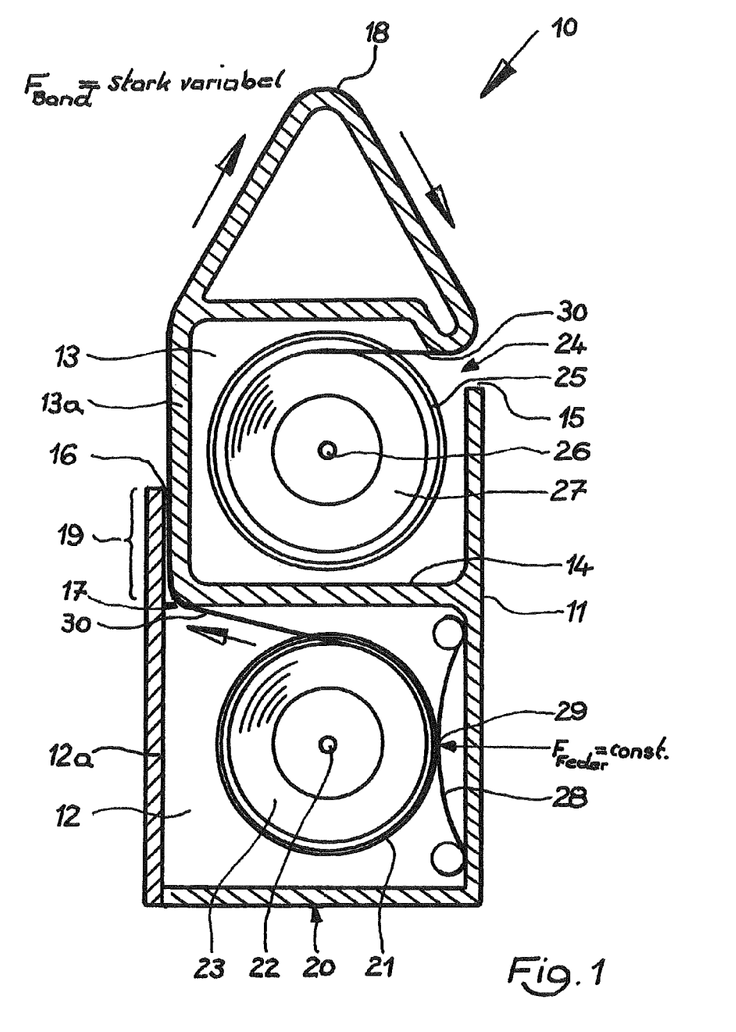
FIG. 1 shows a first embodiment example of a tape magazine according to the invention in cross-section.
Figure 2:
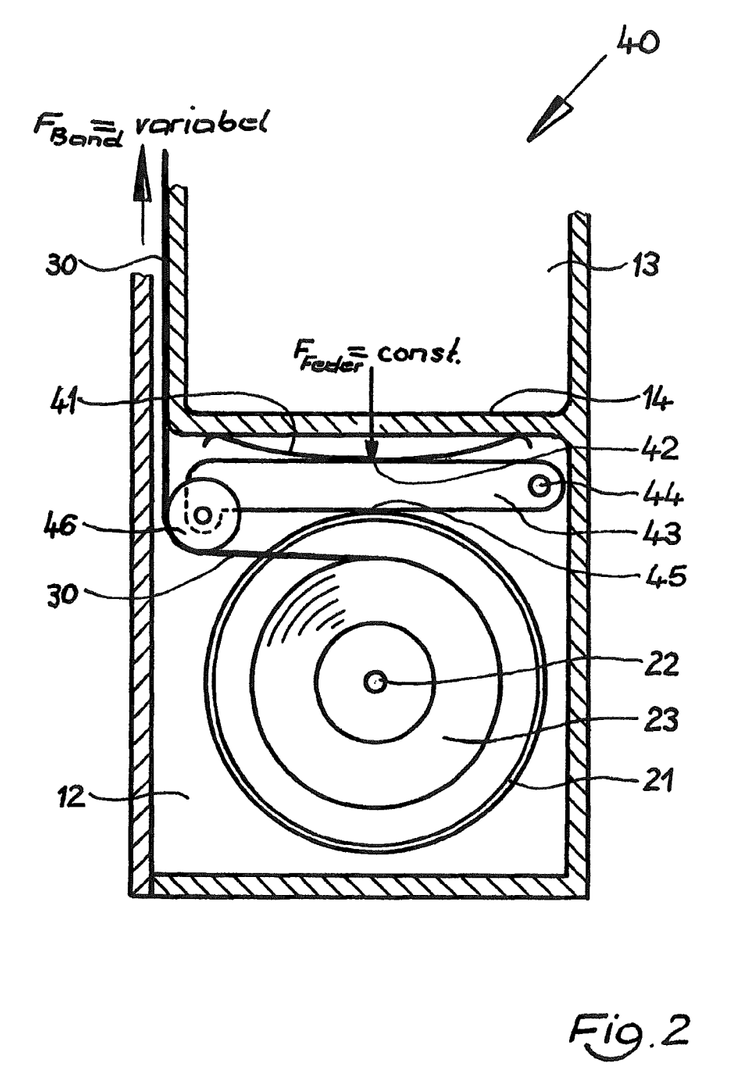
FIG. 2 shows a second embodiment example of a tape magazine according to the invention in a side-view in a partial cross-section.
Figure 3:
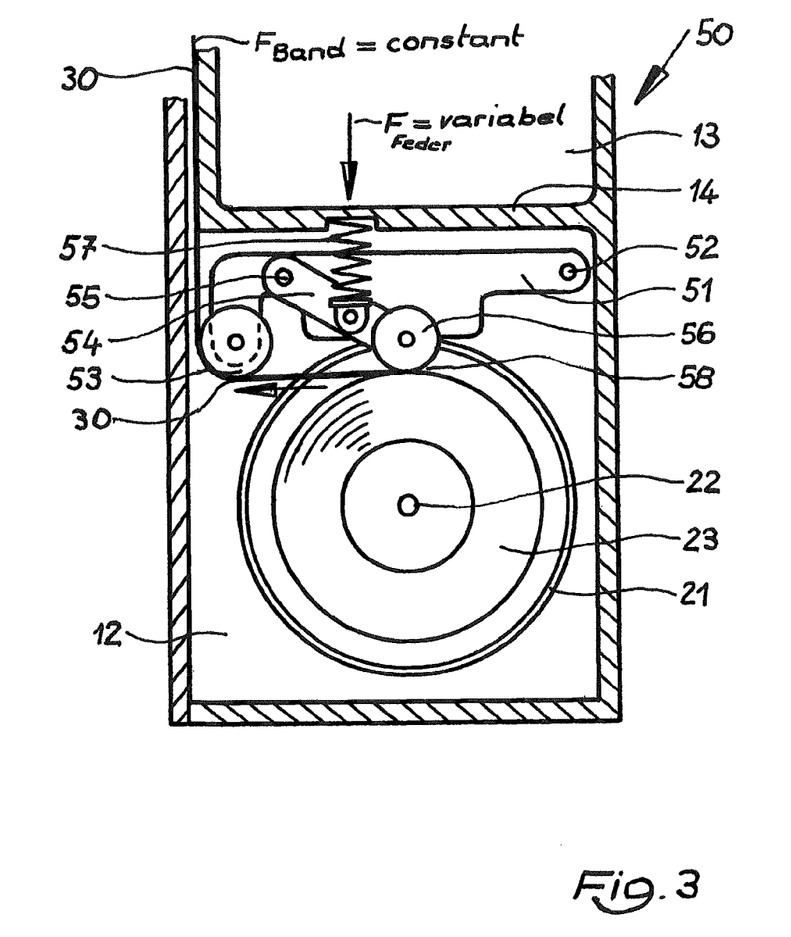
FIG. 3 shows a third embodiment example of a tape magazine according to the invention in a side-view in a partial cross-section.

FIGS. 1 to 3 show various embodiment examples of a tape magazine according to the invention in which the test tape is held under tensile strain. FIG. 1 shows a tape magazine 10 with a housing 11. The housing 11 is divided into a first holder 12 for a storage unit 20 and a second holder 13 for a waste unit 24. The holders 12, 13 are separated from one another by a dividing wall 14 so that the storage unit 20 is separated from the waste unit 24. One side wall 12a, 13a of each of the holders 12, 13 overlaps in the area 19 to form an opening 16 which is provided with a seal 17. The seal 17 can act as a brake, sealing the storage unit 20 at the opening 16 for the test tape 30. Another opening 15 is provided in the holder 13 for the waste unit 24. A deflector head 18 for the test tape 30 is integrated into the housing 10.

The storage unit 20 has a spool or reel housing 21 which holds an unused test tape 30 which is wound around a spool 22 to form a supply spool 23. The waste unit 24 is similarly equipped with a spool housing 25 which holds the used test tape wound onto a spool 26 to form a waste spool 27. The spool 26 is driven by a drive (not shown). The test tape 30 is divided into consecutive test areas. If the drive is actuated, the fresh test tape 30 is wound off the supply spool 23 and guided from the holder 12 through the opening 16 to the deflector head 18 where a single test area comes to rest exposed to the outside and can take up a test liquid such as a drop of blood. The test liquid is measured by a detection unit (not shown). When the drive is actuated again the test tape 30 is transported further. The used test tape 30 passes through the opening 15 into the holder 13 and is wound onto the waste spool 27.

An integrated brake is formed to hold the test tape 30 under tension between the storage and waste units 20, 24. It is within the scope of the present invention that the brake be formed to apply a force to the storage unit 20, to exert a direct braking force on the test tape 30; to act on a reel body 21 for the test tape 30 such that the test tape is indirectly braked, or to exert a constant braking force on the storage unit 20. It is further appreciated that it is within the scope of the present invention that the brake is designed as a frictional element.

It is further appreciated that the brake may be formed to act on the storage unit with a variable braking force in accordance with this disclosure. In such an instance, the variable braking force may depend on the diameter of a tape spool of the storage unit 20. Alternatively, the variable braking force may depend on the tape tensile force upon movement of the test tape 30.

In an embodiment shown in FIG. 1, the brake is a leaf spring 28 as a frictional element which acts upon the contact point 29 of the spool housing 21. The spring 28 is provided on an inner wall of the holder 12 for the storage unit 20. The leaf spring 28 is pretensioned with a constant spring force $F_{spring}$. Therefore, the test tape 30 has to be reeled off against the corresponding brake torque at a certain tape tensile force $F_{tape}$. This tape tensile force increases as the radius of the supply spool 23 decreases.

FIGS. 2 and 3 show two further embodiment examples of a tape magazine 40, 50 according to the invention which only differ from the aforementioned tape magazine 10 with regard to the design of the brake. Hence identical components are labelled with the same reference numerals.

The tape magazine 40 shown in FIG. 2 also has a leaf spring 41 on an inner wall of the holder 12 below the dividing wall 14 which is pretensioned with a constant spring force $F_{spring}$. In addition a rocking lever 43 is hinged around one axis 44 on the inner wall of the holder 12. The free end of the rocking lever 43 is provided with a rotating deflector roller over which the test tape 30 is guided. The rocking lever 43 is arranged between the leaf spring 41 and the spool housing 21 and extends tangentially to the spool housing 21. The rocking lever 43 touches the leaf spring 41 at a contact point 42 and the spool housing 21 at a contact point 45. A constant spring force $F_{spring}$ is applied to the rocking lever 43 by the leaf spring 41. Consequently a corresponding force is also applied to the spool housing 21 by the rocking lever 43.

When the drive for the test tape 30 is actuated, it has to be reeled off at a certain tape tensile force $F_{tape}$ against the brake torque acting on the spool housing 21. The tape tensile force acts upon the long lever arm of the rocking lever 43 via the deflector roller 46 and relieves the contact point 45 depending on the tape tensile force. Hence a lower tape tensile force has to be applied to reel off the test tape than in the case of the embodiment example shown in FIG. 1 as the diameter of the supply spool 23 decreases.

The embodiment example shown in FIG. 3 of a tape magazine 50 is formed to include a compensation mechanism that is loaded with a force that changes depending on the diameter of a tape spool of the storage unit. Tape magazine 50 has a rocking lever 51 on the inner wall of the holder 12 below the dividing wall 14 which is hinged on the inner wall around an axis 52. The free end of the rocking lever 43 is also provided with a rotating deflector roller 53 over which the test tape 30 is guided. The rocking lever 51 also extends tangentially to the spool housing 21 and touches the spool housing 21 at a contact point that is not visible in the figure.

The compensation mechanism is formed by a rocker arm 54 that can rotate around an axis 55 is pivoted on the rocking lever 51. The free end of the rocker arm 54 is provided with a follower roller 56 which rests on the circumference of the supply spool 23 at a contact point 58. A pressure spring 57 which is pretensioned with a certain spring force $F_{spring}$ is braced against the dividing wall 14 and the rocker arm 54 such that this spring force is applied to the rocker arm 54.

When the drive for the test tape 30 is actuated, it has to be reeled off with a certain tape tensile force $F_{tape}$ against the brake torque acting on the spool housing 21. This tape tensile force acts upon the long lever arm of the rocking lever 43 and relieves the contact point between the rocking lever 51 and the spool housing 21 depending on the tape tensile force. At the same time the follower roller 56 of the rocker arm 54 runs on the circumference of the supply spool 23. As the radius of the supply spool 23 decreases, the follower roller 56 travels towards the spool 22 so that the pressure spring 57 relaxes as the radius of the supply spool 23 decreases. Thus the contact point between the rocking lever 51 and the spool housing 21 is relieved as a function of the radius of the supply spool 23. As a result the tape tensile force $F_{tape}$ that has to be applied by the drive remains constant as the radius of the supply spool 23 decreases.

Figure 4:
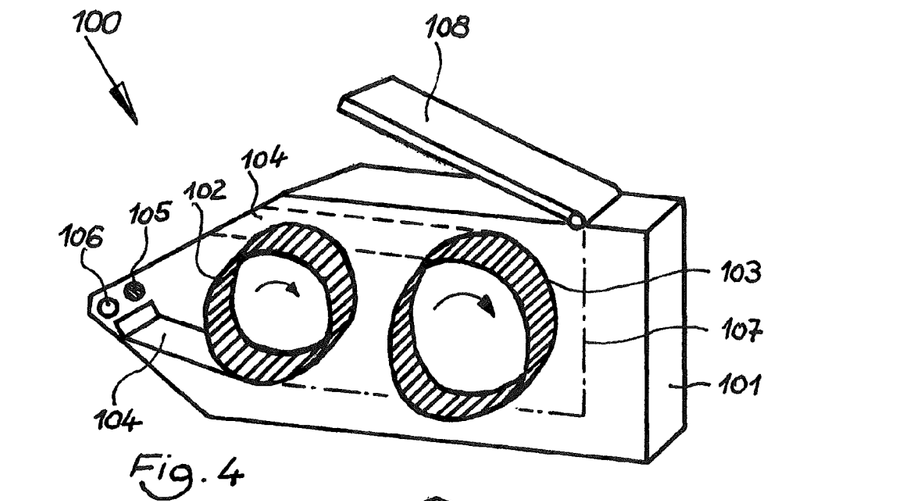
FIG. 4 shows an embodiment example of a mechanically operated tape device in a perspective view with a partially opened housing.
Figure 5:
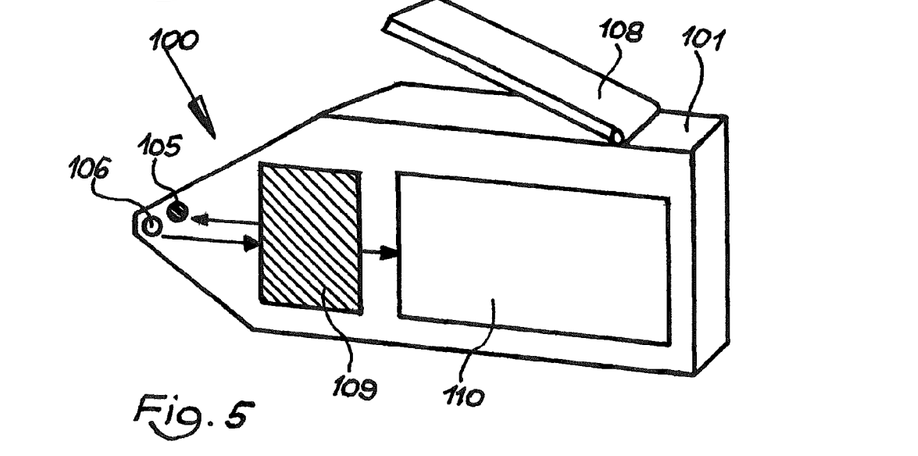
FIG. 5 shows the device according to FIG. 4 with a closed housing.

FIGS. 4 and 5 show a combination of a hand-held device with polymer-based electronic components and a mechanical drive for the test tape.

The hand-held device 100 is a single-use device, a so-called disposable. It has a housing 101 made of plastic in which two reel bodies 102, 103 are located. A test tape 104 with consecutive test fields is wound onto the reel bodies 102, 103. In an embodiment, device electronics are provided that are based upon integrated polymer circuits (IPC). A non-limiting example of which includes a photo-optic sensor 105 provided in the housing 101 in spatial vicinity to a measuring site 106. At the measuring site 106 the test tape 104 is accessible from outside in order to take up a sample liquid such as blood for a blood sugar determination. The area between the emitter and receiver of the sensor and the test tape can be bridged by an optical path or light guide. The measured value recorded by the sensor 105 is transferred to an evaluation unit 109. Here a display value such as the blood sugar content is calculated.

The photo-optical sensor consists of at least one light-emitting diode (LED) of a suitable wavelength, particularly an organic light-emitting diode (OLED), combined with one or more organic photodiodes (multi-photometer principle). LEDs of multiple wavelengths are also conceivable. It is further conceivable that the device may include an electrochemical detection system. In an embodiment, it is appreciated that the electrochemical sensor components are mounted on the test tape 104 and are connected to the device electronics at a measuring position.

The evaluation unit 109 comprises for example an amplifier, analog/digital (AD) converter, calculator, control mechanism, data store, energy supply and interfaces, and is connected to a display unit 110 which shows the determined display value on a display. The display unit can be designed in a known manner such that a display can be maintained until the next measuring process even without an energy supply for example by using so-called "electronic inks".

The data store in the evaluation unit can consist of a read-only memory (ROM) or electrically erasable programmable read-only memory (EEPROM). It is mainly required to store batch-specific data which are determined during the manufacture of the disposables and are deposited thereon. Data transfer occurs by means of contact interfaces or radio-frequency identification (RF-ID) transponders. An electronic test field counter can also be realized using an EEPROM.

The electronic components of this hand-held instrument are known polymer-electronic components. Such components are described in for example in CA 2516490 A1 2004 May 27 the contents thereof being herewith incorporated into the disclosure of the present patent application. The use of such components enables all necessary electronic components to be integrated into a magazine housing so that the resulting tape magazine also constitutes a fully functional and very convenient single-use hand-held device. Such a single-use hand-held device is small and light, cost-effective and easy to operate. It is not necessary to change the tape magazine. It leaves room for further miniaturization of portable hand-held devices. It also obviates the necessity for a complicated construction of interfaces between the tape magazine and hand-held device.

All polymer-based electronic components can be printed in a known manner onto suitable moldings of the housing 101 of the hand-held instrument 100.

The energy is supplied by high-performance capacitors (supercap) for example combined with solar cells/photovoltaic cells. Due to the low-energy density that can be achieved it is recommended to manually drive the spool bodies 102, 103 of the described disposable hand-held device.

A transport mechanism is provided as a tape drive. For this purpose the reel bodies 102, 103 have teeth or steps. A feed pawl 107 which is only indicated here engages in these teeth or steps. The feed pawl 107 is connected to a lever 108 provided on the outside of the housing. The test tape 104 is fed by operating the lever. This moves the reel bodies 102, 103 exactly so far that a fresh test field of the test tape 104 is accessible from outside at the measuring site 106. In order to synchronize the movement of the reel bodies 102, 103 and test tape 104, the latter is perforated such that teeth arranged on the reel bodies 102, 103 (not shown) engage in the perforation. The test fields can also be spaced on the test tape in such a manner that a first operation of the lever 108 makes a fresh test field accessible at the measuring site 106. A second operation of the lever 108 moves the test field which is now used away from the measuring site 106 without a new test field immediately appearing. This only occurs when the lever 108 is operated again.

The operation of the lever 108 can also generate in a known manner the energy of a few milliwatts required for the measurement which can for example be temporarily stored in a capacitor or supercap. A temporary mechanical store in the form of a spring can be provided to obtain energy by a generator or piezoelectrically which allows an adaptation to the various time constants.

A particularly environmentally friendly design of the device can be achieved by refraining from an electrochemical energy store.

The invention claimed is:

1. A method comprising:
   providing a tape magazine that includes test tape, a storage unit with a supply spool around which unused test tape is wound, and a waste unit with a waste spool around which used test tape is wound;

applying a brake force with an integrated brake to hold the test tape under tension between the storage unit and the waste unit;

preventing the used test tape from being removed from the waste unit with a recoil prevention device engaging the waste spool; and driving the waste spool to actuate the test tape with a tensile force sufficient to move the test tape from the storage unit to the waste unit.

2. The method of claim 1 wherein said applying the brake force includes pressing a seal against the test tape to seal the storage unit.

3. The method of claim 1, further comprising:
   wherein the recoil prevention device includes a safety catch and gear teeth on the waste spool; and
   wherein said preventing includes engaging the gear teeth with the safety catch.

4. The method of claim 1 wherein the recoil prevention device includes a recoil locking device to restrict the waste unit to a wind on direction of rotation.

5. The method of claim 1 wherein the recoil prevention device includes a recoil brake.

6. The method of claim 5 wherein the recoil brake includes a wrap spring lock.

7. The method of claim 5 wherein the recoil brake includes a clamp roller free-wheel.

8. The method of claim 1 wherein the integrated brake includes a leaf spring.

9. The method of claim 1 wherein the integrated brake includes a seal sealing the storage unit.

10. The method of claim 1 wherein the integrated brake applies a force to the storage unit.

11. The method of claim 1 wherein the integrated brake exerts a direct braking force on the test tape.

12. The method of claim 1 wherein the integrated brake acts on a reel body for the test tape.

13. The method of claim 1 wherein the integrated brake exerts a constant braking force on the storage unit.

14. The method of claim 1 wherein the integrated brake is formed as a frictional element.

15. The method of claim 1 wherein the integrated brake acts on the storage unit with a variable braking force.

16. The method of claim 15 wherein the variable braking force depends on the diameter of a tape spool of the storage unit.

17. The method of claim 15 wherein the variable braking force depends on the tape tensile force upon movement of the test tape.

18. The method of claim 15 wherein the integrated brake has a lever loaded with a braking force via a spring.

19. The method of claim 18 wherein the lever has a roller at one end and the test tape is deflected over the roller.

20. The method of claim 1 wherein the integrated brake has a compensation mechanism that is loaded with a force that changes depending on the diameter of a supply spool of the storage unit.

21. The method of claim 20 wherein the compensation mechanism is formed by a spring-loaded rocker arm which touches the circumference of the supply spool.

22. The method of claim 1 wherein the storage unit has a first housing wall and the waste unit has a second housing wall that forms an overlapping area with the first wall, the overlapping area defining an opening formed to carry through the test tape.

23. The method of claim 22 wherein the integrated brake includes a seal positioned in the opening.

* * * * *